United States Patent [19]

Eckrich et al.

[11] Patent Number: 4,977,257
[45] Date of Patent: Dec. 11, 1990

[54] DMF SOLVATES OF A BETA-LACTAM ANTIBIOTIC

[75] Inventors: Thomas M. Eckrich; Richard C. Hoying, both of Indianapolis, Ind.

[73] Assignee: Eli Lilly and Company, Indianapolis, Ind.

[21] Appl. No.: 530,140

[22] Filed: May 29, 1990

Related U.S. Application Data

[63] Continuation of Ser. No. 271,545, Nov. 14, 1988, abandoned.

[51] Int. Cl.$^5$ ........................................... C07D 487/04
[52] U.S. Cl. ...................................................... 540/205
[58] Field of Search ......................................... 540/205

[56] References Cited

U.S. PATENT DOCUMENTS

| 3,655,656 | 4/1972 | Van Heyningen | 260/243 C |
|---|---|---|---|
| 3,781,282 | 12/1973 | Garbrecht | 260/243 C |
| 3,819,620 | 6/1974 | Dursch et al. | 260/243 |
| 3,925,372 | 12/1975 | Chauvette | 260/243 C |
| 4,302,541 | 11/1981 | Hirata et al. | 435/119 |
| 4,316,958 | 2/1982 | Hirata et al. | 435/119 |
| 4,335,211 | 6/1982 | Hashimoto et al. | 435/119 |
| 4,708,956 | 11/1987 | Hirata et al. | 514/210 |

FOREIGN PATENT DOCUMENTS

2041923 A  9/1980  United Kingdom .

OTHER PUBLICATIONS

J. Turner et al., "Absorption, Distribution, Metabolism and Elimination of LY163892 (KT 3772), an Orally Absorbed βLactam, in Laboratory Animals", Abstract No. 1204, Twenty-Seventh Interscience Conference on Antimicrobial Agents and Chemotherapy, Oct. 4–7, 1987, Program and Abstracts published Aug. 17, 1987.
Merck Index, 10th edition (1983), Entry 1896 (pp. 267–268).
R. Pfeiffer et al., "Crystal Pseudopolymorphism of Cephaloglycin and Cephalexin," *Journal of Pharmaceutical Sciences,* 59(12), pp. 1809–1814 (1970).

Primary Examiner—Mark L. Berch
Attorney, Agent, or Firm—Joseph A. Jones; Leroy Whitaker

[57] ABSTRACT

The crystalline bis(DMF), dihydrate mono(DMF) and mono(DMF) forms of 7β-[2'-(R)-2'-phenyl-2'-aminoacetamido[-3-chloro-3-(1-carbadethiacephem)-4-carboxylic acid (LY163892) are useful intermediates to the monohydrate form of LY163892.

6 Claims, No Drawings

DMF SOLVATES OF A BETA-LACTAM ANTIBIOTIC

This application is a continuation of application Ser. No. 07/271,545, filed Nov. 14, 1988 abandoned.

BACKGROUND OF THE INVENTION

This invention relates to novel solvate forms of a β-lactam antibiotic, more particularly to novel crystalline bis(DMF), dihydrate mono(DMF) and mono(DMF) forms of a 1-carbacephalosporin.

The β-lactam antibiotic of the Formula I

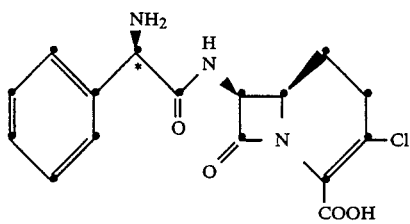

is a potent orally-active antibiotic. The antibiotic is described, for example, by J. Hashimoto et al. in U.S. Pat. No. 4,335,211, issued June 15, 1982. For brevity's sake, the compound of Formula I will be referred to by the Ser. No. LY163892.

The present invention is directed to the crystalline bis(N,N'-dimethylformamide) solvate of LY163892, the crystalline dihydrate mono(N,N'-dimethylformamide) solvate of LY163892 and the crystalline mono(N,N'-dimethylformamide) solvate of LY163892. The three solvates will be referred to hereinafter as the "bis(DMF)", "dihydrate mono(DMF)" and the "mono(DMF)" solvates, respectively. It will be understood that these abbreviated terms refer to the crystalline or microcrystalline form of the three solvates.

The bis(DMF), dihydrate mono(DMF) and mono(DMF) solvates are convenient intermediates to LY163892 in general and to the monohydrate form of LY163892 specifically. LY163892 monohydrate ("monohydrate") is a pharmaceutically elegant hydrate of LY163892. The monohydrate affords a stable, easy-to-handle form of LY163892, a compound that here-to-fore was both difficult to purify and obtain in a pharmaceutically elegant form. The monohydrate also affords a necessary form of LY163892 useful in the manufacture of the various dosage forms of the antibiotic. The monohydrate is disclosed in U.S. Ser. No. 07/105,766, filed Oct. 6, 1987 abandoned, entitled MONOHYDRATE OF NEW BETA-LACTAM ANTIBIOTIC.

SUMMARY OF THE INVENTION

One aspect of the present invention is directed to the crystalline bis(DMF) solvate of LY163892. The formula for LY163892 is given below as Formula I. More specifically, the invention is directed to crystalline LY163892 bis(DMF) having the X-ray powder diffraction pattern listed below in Table 1.

Another aspect of the invention is the crystalline dihydrate mono(DMF) solvate of LY163892. A preferred form of the dihydrate mono(DMF) solvate is a crystalline compound having the X-ray powder diffraction pattern listed below in Table 2.

Yet another aspect of the invention is the crystalline mono(DMF) solvate of LY163892. A preferred form of the mono(DMF) solvate is a crystalline compound having the X-ray powder diffraction pattern set forth in Table 3 below.

DETAILED DESCRIPTION OF THE INVENTION

The instant invention is directed to the crystalline bis(DMF), dihydrate mono(DMF) and mono(DMF) solvates of the compound of Formula I:

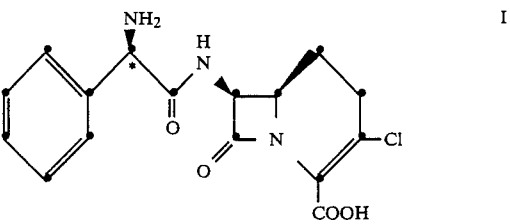

In the present solvates of Formula I the C-2' asymmetric center has the R absolute configuration. Furthermore, the instant solvates may encompass the zwitterionic form of the compound of Formula I.

A preferred embodiment of the invention is a crystalline bis(DMF) solvate of LY163892 exhibiting the X-ray powder diffraction pattern of Table 1:

TABLE 1

| Bis(DMF) Solvate | |
|---|---|
| d | I/I$_1$ |
| 15.23 | .01 |
| 12.27 | 1.00 |
| 10.91 | .04 |
| 7.75 | .01 |
| 5.57 | .02 |
| 5.37 | .05 |
| 4.84 | .02 |
| 4.74 | .09 |
| 4.44 | .03 |
| 4.11 | .30 |
| 3.80 | .03 |
| 3.62 | .03 |
| 3.36 | .01 |
| 3.08 | .04 |
| 2.86 | .01 |
| 2.73 | .02 |

The diffraction pattern in Table 1 was obtained with nickel-filtered copper radiation (Cu:Ni) of wavelength λ=1.5406 Å. The interplanar spacings are in the column marked "d" and are in Angstroms and the relative intensities are in the column marked "I/I$_1$".

Another preferred embodiment of the instant invention is the crystalline dihydrate mono(DMF) solvate of Ly163892 exhibiting the X-ray powder diffraction pattern set forth below in Table 2:

TABLE 2

| Dihydrate Mono(DMF) Solvate | |
|---|---|
| d | I/I$_1$ |
| 15.78 | .03 |
| 12.72 | .03 |
| 11.56 | 1.00 |
| 7.28 | .07 |
| 5.79 | .03 |
| 5.34 | .03 |
| 5.17 | .03 |
| 4.76 | .53 |
| 4.40 | .13 |
| 4.00 | .03 |
| 3.82 | .07 |
| 3.63 | .37 |
| 2.93 | .03 |

TABLE 2-continued

| Dihydrate Mono(DMF) Solvate | |
|---|---|
| d | I/I$_1$ |
| 2.71 | .03 |
| 2.61 | .03 |

The X-ray data in Table 2 was collected employing the same instrument parameters used to collect the data in Table 1.

Another preferred embodiment of the invention is the crystalline mono(DMF) solvate of LY163892 exhibiting the X-ray powder diffraction pattern set forth below in Table 3:

TABLE 3

| Mono(DMF) Solvate | |
|---|---|
| d | I/I$_1$ |
| 14.87 | .07 |
| 11.20 | 1.00 |
| 9.91 | .36 |
| 8.78 | .03 |
| 7.17 | .27 |
| 5.66 | .10 |
| 5.41 | .09 |
| 4.82 | .35 |
| 4.69 | .53 |
| 4.62 | .40 |
| 4.41 | .30 |
| 4.30 | .21 |
| 3.62 | .57 |
| 3.59 | .37 |
| 3.28 | .12 |
| 3.09 | .05 |

The X-ray data in Table 3 was collected employing the same instrument parameters used to collect the data in Table 1 except that λ=1.5418 Å.

The bis(DMF) solvate of LY163892 can be readily prepared by suspending any form of LY163892, for example the anhydrate, ethanol solvate or the like, in aqueous DMF and forming a solution. A solution is most commonly effected by the addition of acid, typically dilute hydrochloric acid, although solution may also be caused by addition of base. The desired bis(DMF) solvate is precipitated by the adjustment of the pH of the solution to approximately 5 to 6 by the addition of acid or base as needed, at a temperature in the range of about 45° C. to about 55° C., most preferably at about 50° C. The precipitated solid is collected, typically by filtration, and vacuum dried to provide the bis(DMF) solvate of the invention.

The dihydrate mono(DMF) solvate of LY163892 is prepared by the same procedure as set forth above except that instead of vacuum drying the collected solid, the solid is air dried.

The three solvates of the present invention may also be prepared by acylating a 7β-amino ("nucleus") compound of the Formula II

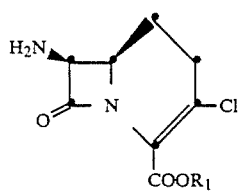

where R$_1$ is a carboxy-protecting group with an acylating agent of the Formula III

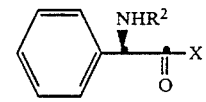

where X is a leaving group and R$_2$ is hydrogen or an amino protecting group, in DMF followed by deprotection. The nucleus and its synthesis are disclosed in U.S. Pat. No. 4,734,494, herein incorporated by reference.

The carboxy-protecting group R$_1$ of Formula II is a conventional carboxy-protecting group and preferably one which is not sterically hindered. Examples of such groups are alkyl, benzyl and substituted benzyl groups such as 4-methoxybenzyl, 4-nitrobenzyl, 4-methylbenzyl, 3,5-dimethylbenzyl, and 4-chlorobenzyl; silyl group such as a trialkylsilyl group (trimethylsilyl); and halo-substituted alkyl groups such as the 2,2,2-trichloroethyl, 2,2,2-tribromoethyl, and 2-iodoethyl groups. A preferred ester group is the benzyl or a substituted benzyl ester group. The amino protecting group R$_2$ of Formula II is selected from either the carbamates such as t-butoxycarbonyl or benzyloxycarbonyl, or the enamines.

In particular, the acylation of the p-nitrobenzyl nucleus compound (R$_1$=para-nitrobenzyl) takes place in cooled (for example, −20° C.) DMF. The acylating agent, an activated derivative of 2-(R)-2-phenyl-2-aminoacetic acid, is added to the cooled DMF. A preferred acylating agent is a compound of the Formula IV

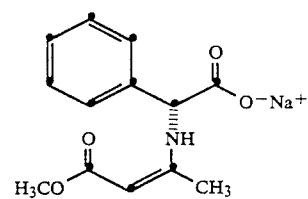

This compound may be prepared according to the procedure of Dane et al. in *Angew. Chem.*, Vol. 74, 873 (1962).

The reaction solution is cooled, and when IV is the acylating agent, methanesulfonic acid, dimethylbenzylamine, and methyl chloroformate are added in rapid succession. The solution is stirred and maintained at a very low (approximately −45° C.) temperature, then the pNB ester of the nucleus is added with stirring. The reaction is stirred at low temperature (for example, −45° C.) until the acylation reaction is substantially complete (as determined by conventional means such as thin layer chromatography). The mixture is then warmed slowly to approximately 0° C. and the reagents for removing the amino and carboxy protecting groups (such as water, concentrated hydrochloric acid, and zinc dust for the pNB ester) are added slowly while maintaining the initial temperature of the solution. The solution is stirred at room temperature until the reaction is complete. In the case where R$_1$ was the pNB ester the pH is raised (for example to 2.3) by the addition of a base such as triethylamine, and the resultant zinc residue is removed by filtration. The pH is gradually taken higher until a white suspension is formed and the pH remains stable without the addition of base (typically around pH 5.6). (The mixture may be seeded with LY163892 at about pH 4.6 to induce crystallization).

The solid phase of the suspension is collected by filtration. The wet filter cake is suspended in a 90:10 mixture of 9:1 DMF/H$_2$O and solution effected with concentrated hydrochloric acid. The solution is cooled and the pH raised in small increments with a base (triethylamine) until a suspension forms and the pH of the solution is stabilized with further additions of base (for example, to a pH of approximately 5.6). The crystals are again collected by filtration and dried to give the bis(DMF) solvate.

Alternatively, the bis(DMF) solvate can be made from a concentrated DMF solution of mono(DMF) solvate. Specifically, anti-solvent (preferably acetonitrile) is added in equal volume to the concentrated DMF solution and the mixture is cooled (for example, to 0° C.). The solid bis(DMF) precipitate is collected by filtration as above.

The methods for the acylation of the 7β-amino compounds of Formula II with an acyl side chain are similar to the methods for the acylation of 6-aminopenicillanic acid, 7-aminodesacetoxycephalosporanic acid, and 7-aminocephalosporanic acid. One method is to simply combine the 7β-amino nucleus with an acid chloride or acid bromide in the presence of an acid scavenger. The acid chloride or acid bromide may be formed in situ. Another method is to combine the 7β-amino nucleus with the free carboxylic acid form of the side chain (or its acid salt) and a condensing agent. Suitable condensing agents include N,N'-disubstituted carbodiimides such as N,N'-dicyclohexylcarbodiimide, N,N'-diethylcarbodiimide, N,N'-di(n-propyl)-carbodiimide, N,N'-di(isopropyl)carbodiimide, N,N'-diallylcarbodiimide, N,N'-bis(p-dimethylaminophenyl)carbodiimide, N-ethyl-N'-(4''-ethylmorpholinyl)carbodiimide, and the like. Other suitable carbodiimide condensing agents are disclosed by Sheehan in U.S. Pat. No. 2,938,892 and by Hofmann et al. in U.S. Pat. No. 3,065,224. Azolides, such as N,N'-carbonyldiimidazole and N,N'-thionyldiimidazole, may also be used as condensing agents. Dehydrating agents such as phosphorus oxychloride, the alkoxyacetylenes, and 2-halogenopyridinium salts (such as 2-chloropyridinium methyl iodide, 2-fluoropyridinium methyl iodide, and the like) may be used to couple the free acid or its acid salt with the 7β-amino nucleus.

Another acylation method entails first converting the free carboxylic acid form (or the corresponding salt) of the acyl side chain to the corresponding active ester derivative, which is in turn used to acylate the nucleus. The active ester derivative is formed by esterifying the free acid form with groups such as p-nitrophenol, 2,4-dinitrophenol, trichlorophenol, pentachlorophenol, 2-chloro-4,6-dimethoxytriazene, N-chlorosuccinimide, N-chloro maleic imide, N-chlorophthalimide, 1-hydroxy-1H-benzotriazole or 1-hydroxy-6-chloro-1H-benzotriazole. The active ester derivatives can also be mixed anhydrides, which are formed with groups such as methoxycarbonyl, ethoxycarbonyl, isobutoxycarbonyl, trichloromethylcarbonyl, and isobut-2-ylcarbonyl, and the carboxylic acid of the acyl side chain. The mixed anhydrides are synthesized by acylating the carboxylic acid of the acyl side chain.

Alternatively, the 7β-amino nucleus can be acylated with the N-ethoxycarbonyl-2-ethoxy-1,2-dihydroquinoline (EEDQ) derivative of the acyl side chain. In general, the free acid form of the acyl side chain and EEDQ are reacted in an inert, polar organic solvent (such as tetrahydrofuran, acetonitrile, and the like). The resultant EEDQ derivative is used in situ to acylate the 7β-amino nucleus.

Yet another method of acylating the 7β-amino compounds entails the use of an enzymatically-assisted process. Such a process is described in Hashimoto et al., U.S. Pat. No. 4,335,211, issued June 15, 1982, herein incorporated by reference.

A preferred method of acylation in general is to first silylate the nucleus with, for example, N,N'-bis(trimethylsilyl)urea (BSU) in DMF. The DMF solution is cooled to a low temperature (−45° C. to −50° C.) then pyridine and the hydrochloride salt of the acid chloride derivative of phenylglycine are added. The acylation is quenched by the addition of strong (5 or 6N) hydrochloric acid, and filtered. The acylated product is then recovered by adjusting the pH of the reaction solution to approximately 6 (more preferably 6.1) by the addition of a base such as triethylamine. The solution is usually seeded with a small amount of LY163892 (such as the mono DMF dihydrate form) after the initial addition of triethylamine. The crystals are collected by filtration. Further details on these and other procedures for the acylation are given below in the Experimental Section.

The amino- and carboxy-protecting groups are removed by methods well known in the art. Examples of conditions for the removal of these two types of protecting groups can be found in standard works on the subject, such as E. Haslam, "Protective Groups in Organic Chemistry", J. G. W. McOmie, Ed., Plenum Press, New York, N.Y., 1973, Chapters 2 and 5, and T. W. Greene, "Protective Groups in Organic Synthesis", John Wiley and Sons, New York, N.Y., 1981, Chapters 5 and 7, respectively.

As noted above, LY163892 bis(DMF), dihydrate mono(DMF) and mono(DMF) solvates are useful as intermediates to LY163892 monohydrate. The monohydrate is prepared by first suspending any of the above starting materials in water. The most common procedure is to effect solution of the starting material by the addition of a minimum amount of acid, generally 6N (or more dilute) hydrochloric acid. Alternatively, a solution of the starting material is effected by adding the minimum amount of base (for example, the minimum amount of 2N sodium hydroxide, resulting in a pH of about 7.6).

Regardless of how solution is effected, crystallization is induced by slowly adjusting the pH of the solution of starting material to approximately 4, and preferably 4.8. For example, if the solution is effected by the addition of acid, it is preferred to raise the temperature of the solution to about 50° C. and slowly add triethylamine (alternatively, sodium hydroxide) to the solution until a pH of approximately 4.8 is obtained. The gradually developing suspension is stirred and maintained at about 50° C. during the addition of the base. Seeding the solution with a small amount of crystalline monohydrate early in the addition period of base is preferred. For example, seeding is often done when the pH of the solution is approximately 1.8. If the starting material solution was effected by the addition of base, the pH is slowly taken to approximately 4 by the addition of an acid (preferably 2N hydrochloric acid). Effecting solution of the starting material with hydrochloric acid and inducing crystallization by adjusting the pH of the solution to approximately 4.8 with triethylamine is preferred.

The suspension resulting from adjusting the pH of starting material solution to approximately 4 is isolated by conventional filtering techniques, such as vacuum filtration on a Büchner funnel. The collected crystals are washed and allowed to dry in air at ambient temperature. Alternatively, the warm pH-adjusted suspensions (50° C.) are cooled to approximately 20° C., stirred, filtered (such as on Büchner funnel) and the collected solid dried at 30° C. for 24 to 48 hours by conventional means (such as a cleaned-air oven).

In the following Examples, the terms dimethylformamide, nuclear magnetic resonance spectra, mass spectrum and infrared spectroscopy are abbreviated DMF, NMR, MS and IR, respectively.

In conjunction with the NMR spectra, the following abbreviations are used: "s" is singlet, "d" is doublet, "t" is triplet, "q" is quartet, and "m" is multiplet.

The NMR spectra were obtained on a General Electric QE-300 300 MHz instrument. The chemical shifts are expressed in ppm values (parts per million downfield from tetramethylsilane).

EXPERIMENTAL SECTION

Example 1

Synthesis of LY163892 Dihydrate Mono(DMF)

To a stirred suspension of 30 g (138.5 mmol) of 7β-amino-3-chloro-3-(1-carba1-dethiacephem)-4-carboxylic a cid in 420 ml of DMF at 23° C. under a nitrogen atmosphere was added 0.1 ml of chlorotrimethylsilane and 36.7 g (180 mmol) of N,N'-bis(trimethylsilyl)urea. The mixture became homogeneous within 15 minutes and was stirred for 30 minutes at 23° C. The solution was cooled to about −55° C. to about −60° C. and pyridine (11.83 g, 12.1 ml, 149.6 mmol) was added followed by portionwise addition (over 5 minutes) of 2-(R)-2-phenyl-2-aminoacetyl chloride. The mixture was warmed to about −33° C. over 30 minutes and held for 75 minutes. Methanol (8.17 ml) was added and the solution was warmed to 0° C. Water (45 ml) was added followed by enough triethylamine to raise the pH to about 3.2. The mixture was filtered on glass paper, warmed to room temperature, and the pH was adjusted to 4.12. After stirring for one hour at 26° C., the pH of the thick suspension was adjusted to about 5.75 over one hour. The suspension was filtered and washed with 10% aqueous DMF. The product was air dried for 12 hours. The solid was slurried in 500 ml of 10% aqueous DMF for 5 hours at 25° C., filtered, washed with 10% aqueous DMF and air dried at 40° C. to a constant weight of 52.95 g (83.3% yield).

H-NMR ($D_2O$/DCL): 8.05 ppm (s, 1H); 7.48 (s,5H); 5.34 (d, 1H); 5.23 (s, 1H); 3.92 (d of t, 1H); 3.05 (s, 3H); 2.91 (s, 3H); 2.55 (m, 2H); 1.62 (m, 1H); 1.31 (m, 1H).

Example 2

Synthesis of LY163892 Mono(DMF)

To a solution of 30 g (138.5 mmol) of 7β-amino-3-chloro-3-(1-carba-1-dethiacephem)-4-carboxylic acid in 500 ml of DMF containing 0.03% water was added approximately 10 drops of trimethylsilyl chloride followed by 32.85 g of N,N'-bis(trimethylsilyl)urea. The reaction mixture was stirred for 90 minutes at room temperature and cooled to approximately −50° C. To the mixture was added 10.8 ml (10.6 g, 122.7 mmol) of pyridine followed by 27.07 g (131.5 mmol) of 2-(R)-2-phenyl-2-aminoacetyl chloride hydrochloride. The mixture was stirred at about −35° C. for approximately one hour and cooled to −50° C. To the mixture was added 7.32 ml of methanol in 30 ml of DMF. The reaction mixture was stirred to 0° C. over a period of 40 minutes and 54 ml of water was added. The reaction mixture was allowed to warm to about 15° C. over the next 30 minutes and triethylamine was slowly added until the pH of the mixture was about 3.2. The filtrate was warmed to about 50° C. To the mixture was added triethylamine until the pH reached 4.6 and the mixture was allowed to stand at room temperature for one hour. The mixture was then stirred at about 40° C. and a mixture of DMF: triethylamine (1:1,v:v) was added until the pH was about 5.9. The mixture was cooled to 25° C. and stirred for 20 minutes. To the mixture was added 500 ml of acetonitrile and the resulting mixture was stirred for 30 minutes. The mixture was filtered and the precipitated solid was dried in an air oven at 30° C. until the weight of the solid was constant to provide LY163892 mono(DMF).

H-NMR (300 MHz, $D_2O$/DCl): 8.18 ppm (s, 1H); 7.79 (s,1H); 5.65 (d, J=4.8 Hz, 1H); 5.51 (s, 1H); 4.21 (d of t, 1H); 3.28 (s, 3H); 3.12 (s, 3H); 2.84 (m, 2H); 1.95 (m, 1H); 1.58 (m, 1H).

$^{13}$C-NMR (75.48 MHz, $D_2O$/DCl): 21.99, 31.85, 32.27, 37.77, 53.47, 57.37, 58.57, 123.5, 128.9, 130.6, 131.4, 132.5, 133.8, 164.4, 165.7, 166.3, 169.9 ppm.

IR (KBr disc): 2950–3620 cm$^{-1}$, (m and broad) 1772.7, 1691.7, 1658.9, 1598, 1566, 1409, 1389, 1378, 1349, 1325 (all medium to strong).

$[\alpha]_D^{20}$ = +17.85°, c=1.02 in 0.1 N HCl.

MS=350, 352

Example 3

Synthesis of LY163892 bis(DMF)

Powdered sodium 2-(R)-2-phenyl-2-(((Z)-methyl but-2-en-3-yloate)amino)acetate (4.59 g, 16.92 mmol) was sifted into a 250 ml round bottom flask containing 75 ml of stirred DMF under a nitrogen atmosphere. Next 22 μl of methanesulfonic acid was added to the reaction mixture which was cooled to about −45° C. To the mixture was added 47.6 μl of dimethylbenzylamine followed by 1.53 g (1.25 ml, 16.15 mmol) of methyl chloroformate. The reaction mixture was stirred at about −45° C. for approximately 50 minutes. To the mixture was added a solution of 25 ml of DMF and 5.41 g (15.38 mmol) of 7β-amino-3-chloro-3-(1-carba-1-dethiacephem)-4-carboxylic (4-nitrophenyl)methyl ester dropwise to the reaction mixture. The mixture was stirred for two hours and warmed to about 0° C. for approximately 45 minutes. While maintaining the temperature of the reaction mixture between about 5° C. and 10° C., 6.89 ml of water, 12.32 ml of concentrated hydrochloric acid, 3.55 g of zinc dust and 8.93 ml of concentrated hydrochloric acid were added to the reaction mixture. The mixture was stirred at room temperature for about five hours and the pH was adjusted to 2.35 with triethylamine. The mixture was filtered and the pH was again adjusted to 4.6 with triethylamine. The mixture was stirred for 45 minutes and the pH was raised to 5.75 with triethylamine. The mixture was stirred for an additional 15 minutes. The precipitated solid was collected by vacuum filtration and washed with 30 ml of DMF:water (9:1, v:v). The solid was vacuum dried for approximately 10 hours to provide 4.8 g of the bis(DMF) solvate of LY163892.

This material was further purified by suspending the material in 40 ml of DMF:water (9:1, v:v). The solution was cooled to 10° C. and the pH was adjusted to 1.7 with concentrated hydrochloric acid. The mixture was filtered and the pH was raised to 5.6 with triethylamine. The precipitated solid was collected by vacuum filtration, washed with DMF:water (9:1, v:v) and vacuum dried at 26° C. to provide 3.72 g of bis(DMF) LY163892.

H-NMR (300 MHz, D$_2$O/DCl): 8.18 ppm (s, 2H); 7.79 (s,1H); 5.65 (d, 1H); 5.51 (s, 1H); 4.21 (d of t, 1H); 3.28 (s, 6H); 3.12 (s, 6H); 2.84 (m, 2H); 1.95 (m, 1H); 1.58 (m, 1H).

IR (KBr disc): 1772.7 cm$^{-1}$, 1691.7, 1659.9, 1599.1, 1566.3, 1407.2, 1389.8, 1378.2, 1349.3, 1325.2 (all medium to strong)

$[\alpha]_D^{20} = +12.68°$, c=0.35 in 0.01 N HCl.

MS=350, 352

Example 4

Conversion of LY163892 bis(DMF) Solvate to LY163892 Monohydrate

The pH of a suspension of 4.0 g of bis(DMF) LY163892 in water was adjusted to 1.57 with concentrated hydrochloric acid. This mixture was seeded with LY163892 monohydrate. The pH was adjusted to approximately 4.9 while maintaining the temperature of the mixture at approximately 50° C. The mixture was cooled to room temperature and the precipitated solid was collected by vacuum filtration, washed with 6 ml of water and air dried. An X-ray powder diffraction pattern of the isolated product was identical to an authentic reference standard. Karl Fischer analysis: 4.36% moisture

Example 5

Conversion of LY163892 Dihydrate mono(DMF) to LY163892 Monohydrate

Water (9.75 l) was filtered into a flask then hydrochloric acid (275 ml, 12 M) was added and the solution was stirred at 20° C. for 10 minutes. 7$\beta$-[2'-(R)-2'-phenyl-2'-aminoacetamido]-3-chloro-3-(1-carba-1-dethiacephem)-4-carboxylic acid, dihydrate mono(DMF) (1465.0 g) was added and the resultant suspension was stirred for 15 minutes. Additional hydrochloric acid (27.5 ml, 12 M) was added to the suspension and the suspension was stirred for 20 minutes to effect solution. Carbon black (Darco ® G60, 750 ml, approximately 250 g) was added to the solution and the resultant suspension was stirred at 24° C. for 30 minutes. The suspension was filtered on a 18.5 cm Büchner funnel containing glass fiber paper and HYFLO ® filter aid. The filtered solution was passed over HYFLO ® filter aid once more as it was added to the flask and the HYFLO ® was rinsed with water (600 ml). The solution was again filtered on a Büchner funnel (11 cm) lined with glass fiber paper. The filtered solution was passed through HYFLO ® filter aid and then heated to 47° C. over a period of 55 minutes. The pH of the solution was raised slowly to pH of 1.55 by the dropwise addition of triethylamine over a period of 35 minutes. This solution was seeded with 100 mg of LY163892 monohydrate. The pH of the seeded solution was raised to 1.8 by the slow addition of triethylamine and the solution was stirred slowly for 1.25 hours. Again, the pH of the solution was raised slowly to 4.8 with stirring while maintaining a temperature of about 50° C. The resultant slurry was stirred for an additional 15 minutes and cooled to 20° C. The slurry was filtered on two 32 cm Büchner funnels containing polypropylene pads over a 30 minute period. The filter in each of the two Büchner funnels was washed with filtered, purified water (500 ml) by first cutting the vacuum to the funnels, allowing the wash to stand for 10 minutes then pulling through the wash by the reapplication of the vacuum. Two washes on each filter were performed. The filters were covered and vacuum was applied for 12 hours. The dried cakes were placed in a cleaned air oven and dried at 30° C. for 48 hours to give 894.5 g, 74.3% yield of crystalline LY163892 monohydrate.

We claim:

1. A crystalline bis (N,N'-dimethylformamide) solvate form of the compound of the Formula I

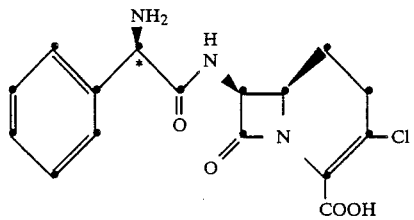

2. A compound of claim 1, which has the following X-ray powder diffraction pattern obtained with a nickel-filtered copper radiation of $\lambda = 1.5406$ Å wherein d represents the interplanar spacing and I/I$_1$ the relative intensity:

| d | I/I$_1$ |
| --- | --- |
| 15.23 | .01 |
| 12.27 | 1.00 |
| 10.91 | .04 |
| 7.75 | .01 |
| 5.57 | .02 |
| 5.37 | .05 |
| 4.84 | .02 |
| 4.74 | .09 |
| 4.44 | .03 |
| 4.11 | .30 |
| 3.80 | .03 |
| 3.62 | .03 |
| 3.36 | .01 |
| 3.08 | .04 |
| 2.86 | .01 |
| 2.73 | .02 |

3. A crystalline dihydrate mono N,N'-dimethylformamide) solvate form of the compound of the Formula I:

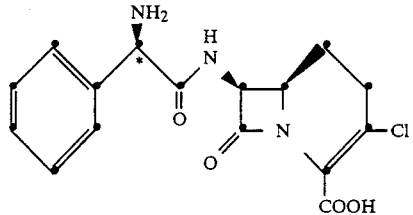

4. A compound of claim 3, which has the following X-ray powder diffraction pattern obtained with a nickel-filtered copper radiation of $\lambda = 1.5406$ Å wherein d represents the interplanar spacing and I/I$_1$ the relative intensity:

5. A crystalline mono(N,N'-dimethylformamide) solvate form of the compound of Formula I:
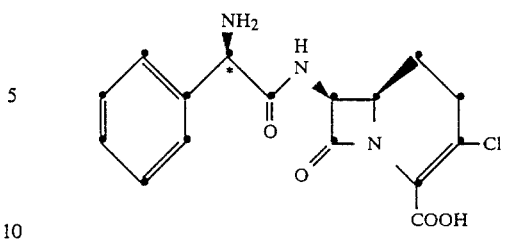
6. A compound of claim 5, which has the following X-ray powder diffraction pattern obtained with a nickel-filtered copper radiation of $\lambda = 1.5418$ Å wherein d represents the interplanar spacing and $I/I_1$ the relative intensity:
| d | $I/I_1$ |
|---|---|
| 15.78 | .03 |
| 12.72 | .03 |
| 11.56 | 1.00 |
| 7.28 | .07 |
| 5.79 | .03 |
| 5.34 | .03 |
| 5.17 | .03 |
| 4.76 | .53 |
| 4.40 | .13 |
| 4.00 | .03 |
| 3.82 | .07 |
| 3.63 | .37 |
| 2.93 | .03 |
| 2.71 | .03 |
| 2.61 | .03 |
| d | $I/I_1$ |
|---|---|
| 14.87 | .07 |
| 11.20 | 1.00 |
| 9.91 | .36 |
| 8.78 | .03 |
| 7.17 | .27 |
| 5.66 | .10 |
| 5.41 | .09 |
| 4.82 | .35 |
| 4.69 | .53 |
| 4.62 | .40 |
| 4.41 | .30 |
| 4.30 | .21 |
| 3.62 | .57 |
| 3.59 | .37 |
| 3.28 | .12 |
| 3.09 | .05 |
* * * * *